(12) United States Patent
Lee et al.

(10) Patent No.: US 7,192,709 B2
(45) Date of Patent: Mar. 20, 2007

(54) METHODS FOR IDENTIFICATION, ASSESSMENT, PREVENTION, AND THERAPY OF CANCER

(75) Inventors: Yi-Chao Lee, Taipei (TW); Pui-Yee Yuen, Taipei (TW); Yi-Huei Huang, Taichung (TW); Hui-Chuan Wu, Taipei (TW)

(73) Assignee: DigiGenomics Co., Ltd., Taipei (TW)

( * ) Notice: Subject to any disclaimer, the term of this patent is extended or adjusted under 35 U.S.C. 154(b) by 212 days.

(21) Appl. No.: 10/801,292

(22) Filed: Mar. 15, 2004

(65) Prior Publication Data

US 2005/0202448 A1 Sep. 15, 2005

(51) Int. Cl.
*C12Q 1/68* (2006.01)

(52) U.S. Cl. .......................................... 435/6; 536/23.1
(58) Field of Classification Search ...................... 435/6
See application file for complete search history.

(56) References Cited

U.S. PATENT DOCUMENTS

| | | | |
|---|---|---|---|
| 4,806,494 | A | 2/1989 | Pastan et al. |
| 6,048,528 | A | 4/2000 | Dunbar |
| 6,258,942 | B1 | 7/2001 | O'Brien et al. |
| 6,350,615 | B1 | 2/2002 | Kaufman et al. |
| 6,468,546 | B1 | 10/2002 | Mitcham et al. |
| 6,468,758 | B1 | 10/2002 | Benson et al. |
| 6,509,458 | B1 | 1/2003 | Afar et al. |
| 6,528,253 | B1 | 3/2003 | Mitcham et al. |
| 6,613,515 | B1 | 9/2003 | Xu et al. |
| 6,617,109 | B1 | 9/2003 | Xu et al. |
| 6,699,664 | B1 | 3/2004 | Mitcham et al. |
| 6,710,170 | B2 | 3/2004 | Xu et al. |
| 6,720,146 | B2 | 4/2004 | Stolk et al. |
| 2003/0143648 | A1 | 7/2003 | Cravatt et al. |
| 2004/0002067 | A1 | 1/2004 | Erlander et al. |

OTHER PUBLICATIONS

Drexler et al (Leukemia and Lymphoma, 1993, 9:1-25).*
Zellner et al (Clin. Can. Res., 1998, 4:1797-17802).*
Hsu (in Tissue Culture Methods and Applications, Kruse and Patterson, Eds, 1973, Academic Press, NY, see abstract, p. 764).*
Slamon et al, (Cancer Cells, 1989, 7:371-384).*
Beck et al (Gynecol Oncol, 1994, 53:196-201).*
Strausberg et al (PNAS, 2002, 99:16899-16903).*
F. S. Collins, "Generation and Initial Analysis of More Than 15,000 Full-Length Human and Mouse cDNA Sequences", PNAS, Dec. 24, 2002, vol. 99, No. 26, pp. 16899-16903.
A. Yamashita, et al., "Characterixation of Solt, a Novel SoxLZ/Sox6 Binding Protein Expressed in Adult Mouse Testis", FEBS Letters 481, (2000), pp. 147-151.
G. Merla, et al., "Identification of Additional Transcripts in the William-Beuren Syndrome Critical Region", Hum Genet (2002) 110:429-438.
X. Fang et al., "Lysophospholipid Growth Factors in the Initiation, Progression, Metastases, and Management of Ovarian Cancer", Annals New York Academy of Sciences, pp. 188-208.
A. Tokumura, "Physiological and Pathophysiological Roles of Lysophosphatidic Acids Produced by Secretory Lysophospholipase D in Body Fluids", Biochimica et Biophysica Acta, 1982, (2002), pp. 18-25.
K. Sawada, et al., "Lysophosphatidic Acid Induces Focal Adhesion Assembly Through Rho/Rho-Associated Kinase Pathway in Human Ovarian Cancer Cells", Gynecologic Oncology 87, 252-259 (2002).

* cited by examiner

*Primary Examiner*—Jeffrey Siew
*Assistant Examiner*—Laura B Goddard
(74) *Attorney, Agent, or Firm*—Cohen Pontani Lieberman & Pavane LLP

(57) ABSTRACT

The present invention relates to the newly identified cancer therapeutic targets and biomarkers. These targets/biomarkers are overexpressed in carcinomas generally, and more specifically to adenocarcinoma and squamous cell carcinoma. The invention provides methods of diagnosis, characterization, and therapy of carcinoma based on the degree of overexpression of the targets/biomarkers.

5 Claims, No Drawings

SEQUENCE LISTING

```
<160> NUMBER OF SEQ ID NOS: 21

<210> SEQ ID NO 1
<211> LENGTH: 2096
<212> TYPE: DNA
<213> ORGANISM: Homo sapiens

<400> SEQUENCE: 1
ctcctctgct cctcgaagaa ggccagggcg gggctgccgc aagttttgac attttcgcag      60
cggagacgcg cgcgggcact ctcgggccga cggctgcggc ggcggccgac cctccagagc     120
cccttagtcg cgccccggcc ctcccgctgc ccggagtccg gcgccacga ggcccagccg      180 cgtcctcccg cgcttgctcg cccggcggcc gcagccatgt cccgggggcc cgaggaggtg     240
aaccggctca cggagagcac ctaccggaat gttatgaac agttcaatcc tgggctgcga      300
aatttaataa acctggggaa aaattatgag aaagctgtaa acgctatgat cctggcagga     360
aaagcctact acgatggagt ggccaagatc ggtgagattg ccactgggtc ccccgtgtca     420
actgaactgg acatgtcct catagagatt tcaagtaccc caagaaaact caacgagagt      480
cttgatgaaa attttaaaaa attccacaaa gagattatcc atgagctgga gaagaagata     540
gaacttgacg tgaaatatat gaacgcaact ctaaaaagat accaaacaga acacaagaat     600
aaattagagt ctttggagaa atcccaagct gagttgaaga gatcagaag gaaaagccaa      660 ggaagccgaa acgcactcaa atatgaacac aaagaaattg agtatgtgga gaccgttact     720
tctcgtcaga gtgaaatcca gaattcatt gcagatggtt gcaaagaggc tctgcttgaa      780
gagaagaggc gcttctgctt tctggttgat aagcactgtg gctttgcaaa ccacatacat     840
tattatcact acagtctgc agaactactg aattccaagc tgcctcggtg gcaggagacc      900
tgtgttgatg ccatcaaagt gccagagaaa atcatgaata tgatcgaaga aataaagacc     960
ccagcctcta ccccgtgtc tggaactcct caggcttcac ccatgatcga gagaagcaat    1020
gtggttagga agattacga cacccttttct aaatgctcac caaagatgcc cccgctcct    1080 tcaggcagag catataccag tcccttgatc gatatgtttta ataacccagc cacggctgcc   1140
ccgaattcac aaagggtaaa taattcaaca ggtacttccg aagatcccag tttacagcga    1200
```

-continued

```
tcagtttcgg ttgcaacggg actgaacatg atgaagaagc agaaagtgaa gaccatcttc   1260

ccgcacactg cgggctccaa caagacctta ctcagctttg cacagggaga tgtcatcacg   1320
ctgctcatcc ccgaggagaa ggatggctgg ctctatggag aacacgacgt gtccaaggcg   1380
aggggttggt tcccgtcgtc gtacacgaag ttgctggaag aaaatgagac agaagcagtg   1440
accgtgccca cgccaagccc cacaccagtg agaagcatca gcaccgtgaa cttgtctgag   1500
aatagcagtg ttgtcatccc cccacccgac tacttggaat gcttgtccat gggggcagct   1560
gccgacagga gagcagattc ggccaggacg acatccacct ttaaggcccc agcgtccaag   1620
cccgagaccg cggctcctaa cgatgccaac gggactgcaa agccgccttt tctcagcgga   1680
gaaaacccct ttgccactgt gaaactccgc ccgactgtga cgaatgatcg ctcggcaccc   1740
atcattcgat gagaggacag ccaaggactc tcccgggcct ctccggttct cccttgcgga   1800
atgatgggcg catcctgtct gccacgtgct gacggtcggg aagcttcagt ggagaggcct   1860
aactctaatg tcgcctgctt aagcaaatca tgcttctctg tttcacgtag ttgggttgac   1920
aagtttctgc ctttaagata aatgagtaat agtctaatga ccagctcagc catttaaaat   1980
attttcttcc tattctgttc aagaaacagt aaacttggtt tcaatcttta aaaaaaaaaa   2040
aaaaaaaaaa aaaaaaaaaa aaaaaaaaaa aaaaaaaaaa aaaaaaaaaa aaaaaa       2096

<210> SEQ ID NO 2
<211> LENGTH: 511
<212> TYPE: PRT
<213> ORGANISM: Homo sapiens

<400> SEQUENCE: 2

Met Ser Arg Gly Pro Glu Glu Val Asn Arg Leu Thr Glu Ser Thr Tyr
  1               5                  10                  15

Arg Asn Val Met Glu Gln Phe Asn Pro Gly Leu Arg Asn Leu Ile Asn
             20                  25                  30

Leu Gly Lys Asn Tyr Glu Lys Ala Val Asn Ala Met Ile Leu Ala Gly
         35                  40                  45

Lys Ala Tyr Tyr Asp Gly Val Ala Lys Ile Gly Glu Ile Ala Thr Gly
     50                  55                  60

Ser Pro Val Ser Thr Glu Leu Gly His Val Leu Ile Glu Ile Ser Ser
 65                  70                  75                  80

Thr His Lys Lys Leu Asn Glu Ser Leu Asp Glu Asn Phe Lys Lys Phe
                 85                  90                  95

His Lys Glu Ile Ile His Glu Leu Glu Lys Lys Ile Glu Leu Asp Val
            100                 105                 110

Lys Tyr Met Asn Ala Thr Leu Lys Arg Tyr Gln Thr Glu His Lys Asn
        115                 120                 125

Lys Leu Glu Ser Leu Glu Lys Ser Gln Ala Glu Leu Lys Lys Ile Arg
    130                 135                 140

Arg Lys Ser Gln Gly Ser Arg Asn Ala Leu Lys Tyr Glu His Lys Glu
145                 150                 155                 160

Ile Glu Tyr Val Glu Thr Val Thr Ser Arg Gln Ser Glu Ile Gln Lys
                165                 170                 175

Phe Ile Ala Asp Gly Cys Lys Glu Ala Leu Leu Glu Glu Lys Arg Arg
            180                 185                 190

Phe Cys Phe Leu Val Asp Lys His Cys Gly Phe Ala Asn His Ile His
        195                 200                 205

Tyr Tyr His Leu Gln Ser Ala Glu Leu Leu Asn Ser Lys Leu Pro Arg
    210                 215                 220
```

-continued

```
Trp Gln Glu Thr Cys Val Asp Ala Ile Lys Val Pro Glu Lys Ile Met
225                 230                 235                 240

Asn Met Ile Glu Glu Ile Lys Thr Pro Ala Ser Thr Pro Val Ser Gly
                245                 250                 255

Thr Pro Gln Ala Ser Pro Met Ile Glu Arg Ser Asn Val Val Arg Lys
            260                 265                 270

Asp Tyr Asp Thr Leu Ser Lys Cys Ser Pro Lys Met Pro Pro Ala Pro
        275                 280                 285

Ser Gly Arg Ala Tyr Thr Ser Pro Leu Ile Asp Met Phe Asn Asn Pro
290                 295                 300

Ala Thr Ala Ala Pro Asn Ser Gln Arg Val Asn Asn Ser Thr Gly Thr
305                 310                 315                 320

Ser Glu Asp Pro Ser Leu Gln Arg Ser Val Ser Val Ala Thr Gly Leu
                325                 330                 335

Asn Met Met Lys Lys Gln Lys Val Lys Thr Ile Phe Pro His Thr Ala
            340                 345                 350

Gly Ser Asn Lys Thr Leu Leu Ser Phe Ala Gln Gly Asp Val Ile Thr
        355                 360                 365

Leu Leu Ile Pro Glu Glu Lys Asp Gly Trp Leu Tyr Gly Glu His Asp
370                 375                 380

Val Ser Lys Ala Arg Gly Trp Phe Pro Ser Ser Tyr Thr Lys Leu Leu
385                 390                 395                 400

Glu Glu Asn Glu Thr Glu Ala Val Thr Val Pro Thr Pro Ser Pro Thr
                405                 410                 415

Pro Val Arg Ser Ile Ser Thr Val Asn Leu Ser Glu Asn Ser Ser Val
            420                 425                 430

Val Ile Pro Pro Pro Asp Tyr Leu Glu Cys Leu Ser Met Gly Ala Ala
        435                 440                 445

Ala Asp Arg Arg Ala Asp Ser Ala Arg Thr Thr Ser Thr Phe Lys Ala
450                 455                 460

Pro Ala Ser Lys Pro Glu Thr Ala Ala Pro Asn Asp Ala Asn Gly Thr
465                 470                 475                 480

Ala Lys Pro Pro Phe Leu Ser Gly Glu Asn Pro Phe Ala Thr Val Lys
                485                 490                 495

Leu Arg Pro Thr Val Thr Asn Asp Arg Ser Ala Pro Ile Ile Arg
            500                 505                 510

<210> SEQ ID NO 3
<211> LENGTH: 1794
<212> TYPE: DNA
<213> ORGANISM: Homo sapiens

<400> SEQUENCE: 3
cacatataat aatagcaact cctggtcgac tgattgacca cttgaaacct ttcgtatttt    60
ccaagtgctg gcaagcgctt cctgcgcagg ccgaggcgac ctggagtttg tgacgctgtg   120
atggtctaga ggctggagat tcaagatctg ggtgccatca ttttctggtt ctgttgatga   180
ccctcttcca ggttacatac agcttacatc ttgcatcctc aagcgttttt cttataaggc   240
taaaaattca caaagcatat atcaatgaat caggaggatc tagatccgga tagtactaca   300
gatgtgggag atgttacaaa tactgaagaa gaacttatta gagaatgtga agaaatgtgg   360
aaagatatgg aagaatgtca gaataaatta tcacttattg aactgaaaac actcaccgat   420
tcaaatgctc agctatcatt gttaattatg caagtaaaat gttaaccgc tgaactcagt    480
```

-continued

```
caatggcaga aaaaaacacc tgaaacaatt cccttgactg aagacgttct cataacatta    540
ggaaaagaag agttccaaaa gctgagacaa gatcttgaaa tggtactgtc cactaaggag    600
tcaaagaatg aaaagttaaa ggaagactta gaaagggaac aacggtggtt ggatgaacag    660
caacagataa tggaatctct taatgtacta cacagtgaat tgaaaaataa ggttgaaaca    720
ttttctgaat caagaatctt taatgaactg aaaactaaaa tgcttaatat aaaagaatat    780
aaggagaaac tcttgagtac cttgggcgag tttctagaag accattttcc tctgcctgat    840
agaagtgtta aaagaaaaa gaaaacatt caagaatcat ctgtaaacct gataacactg    900
catgaaatgt tagagattct tataaataga ttatttgatg ttccacatga tccatatgtc    960
aaaattagtg attccttttg gccaccttat gttgagctgc tgctgcgtaa tggaattgcc   1020
ttgagacatc cagaagatcc aacccgaata agattagaag ctttccatca gtaaaaggat   1080
gttttctttt ttcacacagt aaaaattctt atcattcaag gatattggaa ccacaggact   1140
atttggataa aaaacattat ttgcaaatta atgcgcatag tacttttatt gcaaaatggc   1200
atgtgctgcc atctattatt cattttttaaa tggtcatttc ttattcagtg agtgctttag   1260
tgttttaaac tatatggata agaatgcagg tagataatat tctaggcata aaacatttaa   1320
tgtaccttac ctcatgcaat attctttgga ttctttgttg atttatgata ttgctaatat   1380
aatatttct taaatatat aacaatatct tttatgcatt tgagttccag ctggtgcttc   1440
tttatattta gaattataa tgggaaggtc atttaattta cagatggttt taaaattgag   1500
gtaatatctg aggtggcata atttaaaaat atttagcaaa tttgtttcat atatactgtc   1560
ttatttctag atttgtttaa aattggaata tgaaaaacta atggataaag ctagcataaa   1620
attgatattt tagtttgtat tattaatata tcatgttacc ttatatatta atctactctt   1680
gattctgcta attattacca acaaaattgt attcatgaca ttttattaat cctctgtgaa   1740
ttttctgtaa ataaaattat ttctgaaaat ctctaaaaaa aaaaaaaaa aaaa           1794
```

<210> SEQ ID NO 4
<211> LENGTH: 269
<212> TYPE: PRT
<213> ORGANISM: Homo sapiens

<400> SEQUENCE: 4

```
Met Asn Gln Glu Asp Leu Asp Pro Asp Ser Thr Thr Asp Val Gly Asp
  1               5                  10                  15

Val Thr Asn Thr Glu Glu Glu Leu Ile Arg Glu Cys Glu Glu Met Trp
             20                  25                  30

Lys Asp Met Glu Glu Cys Gln Asn Lys Leu Ser Leu Ile Gly Thr Glu
         35                  40                  45

Thr Leu Thr Asp Ser Asn Ala Gln Leu Ser Leu Leu Ile Met Gln Val
     50                  55                  60

Lys Cys Leu Thr Ala Glu Leu Ser Gln Trp Gln Lys Lys Thr Pro Glu
 65                  70                  75                  80

Thr Ile Pro Leu Thr Glu Asp Val Leu Ile Thr Leu Gly Lys Glu Glu
                 85                  90                  95

Phe Gln Lys Leu Arg Gln Asp Leu Glu Met Val Leu Ser Thr Lys Glu
            100                 105                 110

Ser Lys Asn Glu Lys Leu Lys Glu Asp Leu Glu Arg Glu Gln Arg Trp
        115                 120                 125

Leu Asp Glu Gln Gln Ile Met Glu Ser Leu Asn Val Leu His Ser
    130                 135                 140
```

| Glu | Leu | Lys | Asn | Lys | Val | Glu | Thr | Phe | Ser | Glu | Ser | Arg | Ile | Phe | Asn |
| 145 | | | | 150 | | | | | 155 | | | | | 160 | |

| Glu | Leu | Lys | Thr | Lys | Met | Leu | Asn | Ile | Lys | Glu | Tyr | Lys | Glu | Lys | Leu |
| | | | 165 | | | | | 170 | | | | | 175 | | |

| Leu | Ser | Thr | Leu | Gly | Glu | Phe | Leu | Glu | Asp | His | Phe | Pro | Leu | Pro | Asp |
| | | | 180 | | | | | 185 | | | | | 190 | | |

| Arg | Ser | Val | Lys | Lys | Lys | Lys | Asn | Ile | Gln | Glu | Ser | Ser | Val | Asn |
| | | 195 | | | | | 200 | | | | 205 | | | |

| Leu | Ile | Thr | Leu | His | Glu | Met | Leu | Glu | Ile | Leu | Ile | Asn | Arg | Leu | Phe |
| | 210 | | | | | 215 | | | | | 220 | | | | |

| Asp | Val | Pro | His | Asp | Pro | Tyr | Val | Lys | Ile | Ser | Asp | Ser | Phe | Trp | Pro |
| 225 | | | | | 230 | | | | | 235 | | | | | 240 |

| Pro | Tyr | Val | Glu | Leu | Leu | Leu | Arg | Asn | Gly | Ile | Ala | Leu | Arg | His | Pro |
| | | | | 245 | | | | | 250 | | | | | 255 | |

| Glu | Asp | Pro | Thr | Arg | Ile | Arg | Leu | Glu | Ala | Phe | His | Gln |
| | | | 260 | | | | | 265 | | | | |

<210> SEQ ID NO 5
<211> LENGTH: 1660
<212> TYPE: DNA
<213> ORGANISM: Homo sapiens

<400> SEQUENCE: 5

```
gccaggaaat gccctggagt gtgtgtcacc tgtccaggac gacttgttga ttcccaggag     60
ggccgccttt ccggtctggg tccccgagag gactgccttg ctcacctgtc ccctcggcgc    120
ggccccgggg agctcccgag aggccccggg gatcgctggc cctccgaact ccacagcaat    180
gagcaagttg ggcaagttct ttaaagggg cggctcttct aagagccgag ccgctcccag    240
tccccaggag gccctggtcc gacttcggga gactgaggag atgctgggca agaaacaaga    300
gtacctggaa atcgaatccc agagagaaat cgccctggcc aagaagcacg gcacgcagaa    360
taagcgagct gcattacagg cactaaagag aaagaagagg ttcgagaaac agctcactca    420
gattgatggc acactttcta ccattgagtt ccagagagaa gccctggaga actcacacac    480
caacactgag gtgttgagga acatgggctt tgcagcaaaa gcgatgaaat ctgttcatga    540
aaacatggat ctgaacaaaa tagatgattt gatgcaagag atcacagagc aacaggatat    600
cgcccaagaa atctcagaag catttctca acgggttggc tttggtgatg actttgatga    660
ggatgagttg atggcagaac ttgaagaatt ggaacaggag gaattaaata agaagatgac    720
aaatatccgc cttccaaatg tgccttcctc ttctctccca gcacagccaa atagaaaacc    780
aggcatgtcg tccactgcac gtcgatcccg agcagcatct tcccagaggg cagaagaaga    840
ggatgatgat atcaaacaat ggcagcttg ggctacctaa actaaaacac atttttgata    900
cctaaattaa tgagctatag ataaaatata aaaaatgttt ttaccaagtt cagaagttaa    960
caaagactct gctttataat tatattgaat gaataattgt gttttaagcc tcctaagtaa   1020
aagtaaaaaa ggagtcatgt gcatacatag aatcagtgat ggaggccagg cacggtatct   1080
catgcctata atcccagcac tttgggaggc tgaggcagtt gagaccagga gttcgagtcc   1140
agcctgacca acatgaagaa accctgtctg tactaaaaat acaaaaatta gccggacatg   1200
gtggcaggca cctgtaatcc cagctacttg ggaggctgag tcaggagaat cgcttgagcc   1260
caggagatgg aggttgcagt gagccaagat catgccactg cactccagac tgggcaacag   1320
agggagactc cgtctcaaaa actaaaaaaa aaaatacat ttagtatagc ggggggtggg   1380
ggggagaaat aatgttattt cctatgcgaa tgacgtgtat ccctgtaccc atggtaaatg   1440
```

-continued

```
taaatatact gtgtctcttt tgggagagcc ttttagtaga ggagtcttat atgagtctct    1500
acataagtag tttcacttga gttttgcagt ttgaaatctt aaaggagctt taattgacat    1560
ttattatacc aattaagctt ggaatggggc aatggatgca tttcccaaaa cgtgtgaaag    1620
cactaacagc ttatattgct gaatgagaat ctcctgggtg                         1660
```

<210> SEQ ID NO 6
<211> LENGTH: 233
<212> TYPE: PRT
<213> ORGANISM: Homo sapiens

<400> SEQUENCE: 6

```
Met Ser Lys Leu Gly Lys Phe Phe Lys Gly Gly Ser Ser Lys Ser
 1               5                  10                  15

Arg Ala Ala Pro Ser Pro Gln Glu Ala Leu Val Arg Leu Arg Glu Thr
                20                  25                  30

Glu Glu Met Leu Gly Lys Lys Gln Glu Tyr Leu Glu Asn Arg Ile Gln
            35                  40                  45

Arg Glu Ile Ala Leu Ala Lys Lys His Gly Thr Gln Asn Lys Arg Ala
        50                  55                  60

Ala Leu Gln Ala Leu Lys Arg Lys Arg Phe Glu Lys Gln Leu Thr
    65                  70                  75                  80

Gln Ile Asp Gly Thr Leu Ser Thr Ile Glu Phe Gln Arg Glu Ala Leu
                85                  90                  95

Glu Asn Ser His Thr Asn Thr Glu Val Leu Arg Asn Met Gly Phe Ala
               100                 105                 110

Ala Lys Ala Met Lys Ser Val His Glu Asn Met Asp Leu Asn Lys Ile
           115                 120                 125

Asp Asp Leu Met Gln Glu Ile Thr Glu Gln Gln Asp Ile Ala Gln Glu
       130                 135                 140

Ile Ser Glu Ala Phe Ser Gln Arg Val Gly Phe Gly Asp Asp Phe Asp
145                 150                 155                 160

Glu Asp Glu Leu Met Ala Glu Leu Glu Glu Leu Glu Gln Glu Glu Leu
               165                 170                 175

Asn Lys Lys Met Thr Asn Ile Arg Leu Pro Asn Val Pro Ser Ser Ser
           180                 185                 190

Leu Pro Ala Gln Pro Asn Arg Lys Pro Gly Met Ser Ser Thr Ala Arg
       195                 200                 205

Arg Ser Arg Ala Ala Ser Ser Gln Arg Ala Glu Glu Glu Asp Asp Asp
   210                 215                 220

Ile Lys Gln Leu Ala Ala Trp Ala Thr
225                 230
```

<210> SEQ ID NO 7
<211> LENGTH: 1666
<212> TYPE: DNA
<213> ORGANISM: Homo sapiens

<400> SEQUENCE: 7

```
agcgggcgcg gggctgcgag ctagggcggg agaaggagcg cggggaggac gtaccttgtg     60
agatgcgagc cggccaacag cttgcaagca tgctccgctg acccgagcc tggaggctcc    120 cgcgtgaggg actcggcccc cacggcccta gcttcgcgag ggtgcctgtc gcacccagca    180
gcagcagcgg cggccagggg ggcgccgagc cgaggccgct tccgctttcc tacaggcttc    240
tggacgggga ggcagccctc ccggccgtcg tcttttttgca cgggctcttc ggcagcaaaa    300
```

-continued

```
ctaacttcaa ctccatcgcc aagatcttgg cccagcagac aggccgtgct gacggtggat      360
gctcgtaacc acggtgacag cccccacagc ccagacatga gctacgagat catgagccag      420
gacctgcagg accttctgcc ccagctgggc ctggtgccct cgtcgtcgt tggccacagc       480 atgggaggaa agacagccat gctgctggca ctacagaggg tgagccgccc atgtctgggg      540
cctcctccca ttcagtatat accctgaggg ccctgcaggc aacctgggac tcacatgatc      600
gttggatgac caagttcagg ctccaggagc catgcctgag actccctatg tctgcctaag      660
actggtccca gttcggttct ctcccacagc cagagctggt ggaacgtctc attgctgtag      720
atatcagccc agtggaaagc acaggtgtct cccactttgc aacctatgtg gcagccatga      780
gggccatcaa catcgcagat gagctgcccc gctcccgtgc ccgaaaactg gcggatgaac      840
agctcagttc tgtcatccag gacatggccg tgcggcagca cctgctcact aacctggtag      900
aggtagacgg gcgcttcgtg tggagggtga acttggatgc cctgacccag cacctagaca      960
agatcttggc tttcccacag aggcaggagt cctacctcgg gccaacactc tttctccttg     1020
gtggaaactc ccagttcgtg catcccagcc accaccctga gattatgcgg ctcttccctc     1080
gggcccagat gcagacggtg ccgaacgctg gccactggat ccacgctgac cgcccacagg     1140
acttcatagc tgccatccga ggcttcctgg tctaagagtt gctggcaaga agatggccgg     1200
gcgtggtggc tcatgcctgt aattccagca ctttgggagg ctaaggcggg aggatgactt     1260
gaggccagga gttggagacc agcctggcca acatggtgaa accctgtctc tactaaaaat     1320
acaaaaatta gcctggcgtg gtggtgcaca cctgtaatcc cagctactct ggaggctgag     1380
gcaggagaat cacttgaacc ctggaggcag aggttgcaat gagccgagat cacaccacta     1440
cactccagcc taggcaacag agcaagactc tgtctcaaaa aaacaaaac aaaaaggagg      1500 cacaaaaccc caggcttcaa gtctctgcag cctgctccac atttgggcac agaaggactc     1560
agacaggcac tgtgtgggca cgaggtttta caggggtggt cagacctcag gctttaatga     1620
ataaagacac tactccccaa aaaaaaaaaa aaaaaaaaa aaaaaa                     1666
```

<210> SEQ ID NO 8
<211> LENGTH: 101
<212> TYPE: PRT
<213> ORGANISM: Homo sapiens

<400> SEQUENCE: 8

```
Met Arg Ala Gly Gln Gln Leu Ala Ser Met Leu Arg Trp Thr Arg Ala
 1               5                  10                  15

Trp Arg Leu Pro Arg Glu Gly Leu Gly Pro His Gly Pro Ser Phe Ala
                20                  25                  30

Arg Val Pro Val Ala Pro Ser Ser Ser Gly Gly Arg Gly Gly Ala
            35                  40                  45

Glu Pro Arg Pro Leu Pro Leu Ser Tyr Arg Leu Leu Asp Gly Glu Ala
        50                  55                  60

Ala Leu Pro Ala Val Val Phe Leu His Gly Leu Phe Gly Ser Lys Thr
65                  70                  75                  80

Asn Phe Asn Ser Ile Ala Lys Ile Leu Ala Gln Gln Thr Gly Arg Ala
                85                  90                  95

Asp Gly Gly Cys Ser
            100
```

<210> SEQ ID NO 9
<211> LENGTH: 23

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcttctgctt tctggttgat aag                                            23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gattttctct ggcactttga tg                                             22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaaacactca ccgattcaaa tg                                             22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcttttggaa ctcttctttt cc                                             22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agggcagaag aagaggatga tg                                             22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtgctgggac tataggcatg ag                                             22

<210> SEQ ID NO 15
<211> LENGTH: 20
<212> TYPE: DNA
```

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ctgacggtgg atgctcgtaa                                        20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gtgcctgtct gagtccttct gt                                     22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
aagcactgtg gctttgcaaa c                                      21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
aacactcacc gattcaaatg c                                      21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 19
aagcacugug gcuuugcaaa c                                      21

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 20
aacacucacc gauucaaaug c                                      21

<210> SEQ ID NO 21
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 21
aattctccga acgtgtcacg t                                            21
```

METHODS FOR IDENTIFICATION, ASSESSMENT, PREVENTION, AND THERAPY OF CANCER

FIELD OF THE INVENTION

The field of the invention is cancer, including diagnosis, characterization, and therapy of carcinoma.

BACKGROUND OF THE INVENTION

The increased number of cancer cases reported in the United States, and, indeed, around the world, is a major concern. Currently there are only a handful of treatments available for specific types of cancer, and these provide no absolute guarantee of success. Among them, ovarian cancer is the fifth most common cancer (other than skin cancer) in women. It ranks fifth as the cause of cancer death in women. The American Cancer Society estimates that there will be about 25,580 new cases of ovarian cancer in this country in 2004. About 16,090 women will die of the disease.

Despite advances in the chemotherapy, surgery and supportive care, death rates for this disease have remained constant for nearly two decades (National Cancer Institute. SEER Cancer. Statistics Review 1973–1997, 2001). New diagnostic methods and therapies are thus needed.

SUMMARY OF THE INVENTION

The invention relates to the newly identified cancer therapeutic targets (hereinafter "targets" or "targets of the invention"), which are listed in Table 1. These targets are overexpressed in carcinomas generally, and more specifically to adenocarcinoma and squamous cell carcinoma, including colon, breast, lung, ovary, cervix, and prostate cancers. Table 1 provides the sequence identifiers of the sequences of such marker nucleic acids and proteins listed in the accompanying Sequence Listing.

The invention also relates to the cancer markers (hereinafter "markers" or "markers of the invention"), which are listed in Tables 1. These markers are overexpressed in carcinomas generally, and more specifically to adenocarcinoma and squamous cell carcinoma, including colon, breast, lung, ovary, cervix, and prostate cancers. The invention provides nucleic acids and proteins that are encoded by or correspond to the markers (hereinafter "marker nucleic acids" and "marker proteins", respectively). Tables 1 provide the sequence identifiers of the sequences of such marker nucleic acids and proteins listed in the accompanying Sequence Listing.

The invention also relates to various methods, reagents and kits for diagnosing, staging, prognosing, monitoring and treating carcinoma, including ovarian cancer. In one embodiment, the invention provides a diagnostic method of assessing whether a patient has carcinoma or has higher than normal risk for developing carcinoma, comprising the steps of comparing the level of expression of a marker of the invention in a patient sample and the normal level of expression of the marker in a control, e.g., a sample from a patient without carcinoma. A significantly higher level of expression of the marker in the patient sample as compared to the normal level is an indication that the patient is afflicted with carcinoma or has higher than normal risk for developing carcinoma.

In a preferred diagnostic method of assessing whether a patient is afflicted with carcinoma (e.g., new detection ("screening"), detection of recurrence, reflex testing), the method comprises comparing:

a) the level of expression of a marker of the invention in a patient sample, and b) the normal level of expression of the marker in a control non-cancerous sample.

A significantly higher level of expression of the marker in the patient sample as compared to the normal level is an indication that the patient is afflicted with carcinoma.

The invention also provides diagnostic methods for assessing the efficacy of a therapy for inhibiting carcinoma in a patient. Such methods comprise comparing:

a) expression of a marker of the invention in a first sample obtained from the patient prior to providing at least a portion of the therapy to the patient, and b) expression of the marker in a second sample obtained from the patient following provision of the portion of the therapy.

A significantly lower level of expression of the marker in the second sample relative to that in the first sample is an indication that the therapy is efficacious for inhibiting carcinoma in the patient.

It will be appreciated that in these methods the "therapy" may be any therapy for treating carcinoma including, but not limited to, chemotherapy, radiation therapy, surgical removal of tumor tissue, gene therapy and biologic therapy such as the administering of antibodies and chemokines. Thus, the methods of the invention may be used to evaluate a patient before, during and after therapy, for example, to evaluate the reduction in tumor burden.

In a preferred embodiment, the diagnostic methods are directed to therapy using a chemical or biologic agent. These methods comprise comparing:

a) expression of a marker of the invention in a first sample obtained from the patient and maintained in the presence of the chemical or biologic agent, and b) expression of the marker in a second sample obtained from the patient and maintained in the absence of the agent.

A significantly lower level of expression of the marker in the second sample relative to that in the first sample is an indication that the agent is efficacious for inhibiting carcinoma, in the patient. In one embodiment, the first and second samples can be portions of a single sample obtained from the patient or portions of pooled samples obtained from the patient.

The invention additionally provides a monitoring method for assessing the progression of carcinoma in a patient, the method comprising:

a) detecting in a patient sample at a first time point, the expression of a marker of the invention;

b) repeating step a) at a subsequent time point in time; and c) comparing the level of expression detected in steps a) and b), and therefrom monitoring the progression of the carcinoma in the patient.

A significantly higher level of expression of the marker in the sample at the subsequent time point from that of the sample at the first time point is an indication that the carcinoma has progressed, whereas a significantly lower level of expression is an indication that the carcinoma has regressed.

The invention further provides a diagnostic method for determining whether carcinoma has metastasized or is likely to metastasize in the future, the method comprising comparing:

a) the level of expression of a marker of the invention in a patient sample, and b) the normal level (or non-metastatic level) of expression of the marker in a control sample.

A significantly higher level of expression in the patient sample as compared to the normal level (or non-metastatic level) is an indication that the carcinoma has metastasized or is likely to metastasize in the future.

The invention moreover provides a test method for selecting a composition for inhibiting carcinoma in a patient. This method comprises the steps of:

a) obtaining a sample comprising cancer cells from the patient;

b) separately maintaining aliquots of the sample in the presence of a plurality of test compositions;

c) comparing expression of a marker of the invention in each of the aliquots; and d) selecting one of the test compositions which significantly reduces the level of expression of the marker in the aliquot containing that test composition, relative to the levels of expression of the marker in the presence of the other test compositions.

The invention additionally provides a test method of assessing the carcinogenic potential of a product. This method comprises the steps of:

a) maintaining separate aliquots of cells in the presence and absence of the product; and b) comparing expression of a marker of the invention in each of the aliquots.

A significantly higher level of expression of the marker in the aliquot maintained in the presence of the product, relative to that of the aliquot maintained in the absence of the product, is an indication that the product possesses carcinogenic potential. An example of a known carcinogenic product that increases the risk of ovarian cancer is lysophosphatidic acid.

In addition, the invention further provides a method of inhibiting carcinoma in a patient. This method comprises the steps of:

a) obtaining a sample comprising cancer cells from the patient;

b) separately maintaining aliquots of the sample in the presence of a plurality of compositions;

c) comparing expression of a marker of the invention in each of the aliquots; and d) administering to the patient at least one of the compositions which significantly lowers the level of expression of the marker in the aliquot containing that composition, relative to the levels of expression of the marker in the presence of the other compositions.

In the aforementioned methods, the samples or patient samples comprise cells obtained from the patient. The cells may be found in tumor biopsies.

Definitions

A "marker" is a gene whose altered level of expression in a tissue or cell from its expression level in normal or healthy tissue or cell is associated with a disease state, such as cancer. A "marker nucleic acid" is a nucleic acid (e.g.,—mRNA, siRNA, cDNA, oligonucleotides) encoded by or corresponding to a marker of the invention. Such marker nucleic acids include DNA (e.g., cDNA, oligonucleotides) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein encoded by or corresponding to a marker of the invention. A marker protein comprises the entire or a partial sequence of any of the sequences set forth in the Sequence Listing. The terms "protein" and "polypeptide" are used interchangeably.

The "normal" level of expression or amount of a marker is the level of expression or amount of the marker in el cells of a human subject or patient not afflicted with carcinoma. An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples.

A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

According to the invention, the level of expression or amount of a marker of the invention in a sample can be assessed, for example, by detecting the presence in the sample of: the corresponding marker protein (e.g., a protein having one of the sequences set forth as "SEQ ID NO (2, 4, 6 and 8)" in Table 1, or a fragment of the protein (e.g. by using a reagent, such as an antibody, an antibody derivative, an antibody fragment or single-chain antibody, which binds specifically with the protein or protein fragment).

The corresponding marker nucleic acid (e.g. a nucleotide transcript having one of the nucleic acid sequences set forth as "SEQ ID NO 1, 3, 5 and 7" in Table 1, or a complement thereof, or a fragment of the nucleic acid, e.g. by contacting transcribed polynucleotides obtained from the sample with a substrate having affixed thereto one or more nucleic acids having the entire or a segment of the nucleic acid sequence of any of the SEQ ID NO 1, 3, 5 and 7, or a complement thereof, a metabolite which is produced directly (i.e., catalyzed) or indirectly by the corresponding marker protein.

According to the invention, any of the aforementioned methods may be performed using a plurality (e.g. 2, 3, or more) of cancer markers, including epithelial or other cancer markers known in the art. In such methods, the level of expression in the sample of each of a plurality of markers, at least one of which is a marker of the invention, is compared with the normal level of expression of each of the plurality of markers in samples of the same type obtained from control humans not afflicted with carcinoma. A significantly altered (i.e., increased or decreased as specified in the above-described methods using a single marker) level of expression in the sample of one or more markers of the invention, or some combination thereof, relative to that marker's corresponding normal or control level, is an indication that the patient is afflicted with carcinoma. For all of the aforementioned methods, the marker(s) are preferably selected such that the positive predictive value of the method is at least about 10%.

The methods of the invention have the following uses:

(1) assessing whether a patient is afflicted with carcinoma;

(2) assessing the presence of cancer cells;

(3) making antibodies, antibody fragments or antibody derivatives that are useful for treating cancer and/or assessing whether a patient is afflicted with cancer;

(4) making the DNA fragment including but not restricting the primers, antisense nucleotides, siRNA that are useful for treating cancer and/or assessing whether a patient is afflicted with cancer;

(5) assessing the efficacy of one or more test compounds for inhibiting cancer in a patient;

(6) assessing the efficacy of a therapy for inhibiting cancer in a patient;

(7) monitoring the progression of cancer in a patient;

(8) selecting a composition or therapy for inhibiting cancer in a patient;

(9) treating a patient afflicted with cancer;

(10) inhibiting cancer in a patient;

(11) assessing the carcinogenic potential of a test compound; and

(12) preventing the onset of cancer in a patient at risk for developing cancer.

DETAILED DESCRIPTION OF THE INVENTION

The invention relates to cancer markers associated with the cancerous state of ovarian cells. It has been discovered that the higher than normal level of expression of any of these markers or combination of these markers correlates with the presence of ovarian cancer. Methods are provided for detecting the presence of ovarian cancer in a sample, the absence of ovarian cancer in a sample, the stage of ovarian cancer, and other characteristics of ovarian cancer that are relevant to prevention, diagnosis, characterization, and therapy of ovarian cancer in a patient. The methods of the present invention may similarly apply to detecting the presence of other cancer in a sample, the absence of cancer in a sample, the stage of cancer, and other characteristics of cancer that are relevant to prevention, diagnosis, characterization, and therapy of cancer in a patient.

It is a simple matter for the skilled artisan to determine whether a marker is overexpressed in ovarian cancer cells. For example, expression of a marker of the invention may be assessed by any of a wide variety of well known methods for detecting expression of a transcribed nucleic acid or protein. In a preferred embodiment, expression of marker is assessed using the Real-Time Quantitative RT-PCR. By preparing the ovary RNA from the patients with or without ovarian cancer, the Real-Time Quantitative RT-PCR will be performed through the following protocol using the marker specific primer pairs as listed in Table2 and the Sequence Listing. In brief, first-strand cDNA was synthesized at 50° C. for 60 min, followed by a 10-min denaturation at 95° C. using the proper RT-PCR enzyme kit. PCR reactions were then performed in the same tubes using the following conditions for 40 cycles: 95° C. for 30 s, 60° C. for 30 s, and 68° C. for 60 s.

In another preferred embodiment, immunological methods also could be used to determine the overexpression of a marker of the invention. Using the antibody which specifically recognize the protein of the markers, the skilled artisan could detect the expression of the marker in tissue sample or protein extraction from the patients with or without ovarian cancer. The antibody is derived from the full length protein or short peptide.

The level of expression of a marker in normal (i.e. non-cancerous) human ovarian tissue can be assessed in a variety of ways. In one embodiment, this normal level of expression is assessed by assessing the level of expression of the marker in a portion of ovarian cells which appears to be non-cancerous and by comparing this normal level of expression with the level of expression in a portion of the ovarian cells which is suspected of being cancerous. Alternately, and particularly as further information becomes available as a result of routine performance of the methods described herein, population-average values for normal expression of the markers of the invention may be used. In other embodiments, the 'normal' level of expression of a marker may be determined by assessing expression of the marker in a patient sample obtained from a non-canceraffiicted patient, from a patient sample obtained from a patient before the suspected onset of ovarian cancer in the patient, from archived patient samples, and the like.

To determine whether a target of the invention is a therapeutic target for ovarian cancer, the skilled artisan could inhibit the RNA expression of the targets then detect the survival rate of the ovarian cancer cells. The methods are described as follow. In brief, about $0.75 \sim 2 \times 10^4/cm^2$ ovarian cancer cells (such as TOV-112D cells) are incubated at 37° C. in wells containing growth medium (such as TOV-112D cells; 1:1 mixed medium of MCDB 105 {Sigma-Aldrich, MO, USA} and Medium 199 {Life Technologies, Inc., MD, USA} supplemented with 15% calf serum {Life Technologies, Inc., MD, USA}) under a 5% (v/v) $CO_2$, 95% air atmosphere. The cells are then transfected using a standard transfection mixture comprising 200 nM of target specific siRNA (such as SEQ ID 17, SEQ ID 18) and 2 microliters of Oligofectamine™ (Invitrogen Corporation, CA, USA) per well. The cells are incubated in the transfection mixture for about 5 hours, and then replaced with fresh growth medium. After 48 hr, the cell survival rate was determined by adding MTT (Sigma-Aldrich, MO, USA) to the cell cultures at a final concentration of 1 mg/ml. And after 5 hr incubation at 37° C., the dark crystals formed were dissolved in DMSO and the cell viability was indicated by the amount of crystals which was obtained by measuring the absorbance of the solution at 570/630 nm. The lower survival rate in the target specific siRNA treated cells will be revealed by comparing the survival rate in the cells which treated with negative control siRNA.

Materials and Methods:

Cell Lines and Tissue Samples. The human ovarian papillary serous cystoadenocarcinoma cell line, OC 314, was obtained from the ICLC Animal Cell Lines Database (Servizio Biotecnologie IST, Centro di Biotecnologie, Avanzate L.go R. Benzi, 10, 16132 Genova, Italia). The cells were propagated in RPMI 1640 medium (Life Technologies, Inc., -MD, USA) supplemented with 5% calf serum (Life Technologies, Inc., MD, USA) and 2 mM L-glutamine (Sigma-Aldrich, MO, USA). The other human cell lines including TOV-112D (derived from ovarian endometrioid carcinoma), TOV-21G (derived from ovarian clear cell carcinoma), CC7T/VGH (derived from cervical carcinoma), H184B5H5/M10 (human mammary epithelial cell), T/G HA-VSMC (normal aorta smooth muscle cell) and HFL 1 (lung fibroblast) were obtained from Food Industry Research and Development Institute (331 Shih-Pin Road, Hsinchu, 300 Taiwan R.O.C.). TOV-112D and TOV-21G cells were propagated in the 1:1 mixed medium of MCDB 105 (Sigma-Aldrich, MO, USA) and Medium 199 (Life Technologies, Inc., MD, USA) supplemented with 15% calf serum (Life Technologies, Inc., MD, USA). CC7T/VGH cells were propagated in DMEM (Life Technologies, Inc., MD, USA) supplemented with 10% calf serum (Life Technologies, Inc., MD, USA). H184B5H5/M10 cells were propagated in GIBCO 11900 medium (Life Technologies, Inc., MD, USA) supplemented with 10% calf serum (Life Technologies, Inc.). T/G HA-VSMC cells were propagated in the Ham's F12K medium (HyClone Inc., Logan, Utah, USA) supplemented with 10% calf serum (Life Technologies, Inc., MD, USA), 0.05 mg/ml ascorbic acid (Life Technologies, Inc., MD, USA), 0.01 mg/ml insulin (Sigma-Aldrich, MO, USA), 0.01 mg/ml transferring (Sigma-Aldrich, MO, USA), 10 ng/ml sodium selentine (Sigma-Aldrich, MO, USA), and 0.03 mg/ml endothelial cell growth supplement (Sigma-Aldrich, MO, USA). HFL 1 cells were propagated in Ham's F12K medium (HyClone Inc., UT, USA) supplemented with 10% calf serum (Life Technologies, Inc., MD, USA).

The total RNA of human normal ovary (Catalog number: CR0856) and human ovary tumor (Catalog number: 64011-1) were purchased from Clontech (CA, USA).

Microarray: Two human oligo microarray chips (H04 and H05) were constructed from the oligolibrary of Human Release 1.0 (Compugen Inc., Tel Aviv, Israel) A total of 18861 oligo-probes were presented on these two arrays.

0.25 µg of total RNA of each sample is reversed transcribed into cDNA and further in vitro transcribed into cRNA and labeled with CyDye using Amino Allyl MessageAmp aRNA Kit (Ambion, Texas, USA) according to the manufacturer protocol. cRNA of sample normal ovary was labeled with Cy3 and acts as the reference sample. cRNA of sample ovary tumor was labeled with Cy5 and acts as the experimental sample. 1.5 µg of each labeled aRNA of reference and experimental sample was purified, combined, and mixed 2× hybridization buffer according to the manufacturer protocol before applied on the microarray.

Hybridization was done in dark at 38.5° C. for 16 hours. Hybridization and washing conditions were followed according to the manufacturer protocol of CyScribe First-Strand cDNA Labeling Kit (Amersham Biosciences, England).

Microarray image was scanned using GenePix® 4000B microarray scanner (Axon Instruments, Inc, CA, USA). Image was acquired and analyzed using GenePix® Pro 4.1 software (Axon Instruments, Inc, CA, USA). Image was quality checked and lowess normalized using GeneData Expressionist Refiner v3.0 software (GeneData AG, Basel, Switzerland).

Quantitative real-time reverse transcription-polymerase chain reaction (RT-PCR) assays: Total RNA was extracted from each cell sample using TRI REAGENT (Molecular Research Center, Inc., Ohio, USA) according to the manufacturer protocol. Purified RNA was treated with RNase-free DNase I (Ambion, Texas, USA) to remove residual genomic DNA contamination following the manufacturer's protocol. cDNA synthesis and quantitative real-time RT-PCR was performed using the TITANIUM One-Step RT-PCR kit (Clontech, Palo Alto, Calif., USA) containing SYBR Green I (BioWhittaker Molecular Applications; BMA, Rockland, Me., USA). In brief, first-strand cDNA was synthesized at 50° C. for 60 min, followed by a 10-min denaturation at 95° C. PCR reactions were then perfomed in the same tubes using the following conditions for 40 cycles: 95° C. for 30 s, 60° C. for 30 s, and 68° C. for 60 s. The sequences of primers are listed in Table 2 and Sequence Listing. RT-PCRs were performed in triplicate for each RNA sample for both the gene of interest (target gene) and the reference gene (beta-actin). Real-time fluorescence monitoring and melting curve analysis were performed using Rotor-Gene 3000 (Corbett Research, Sydney, Australia). Negative controls containing no DNA template were included in each experiment. A melting curve was created at the end of PCR cycle to confirm that a single product was amplified. Data were analyzed by Rotor-Gene 3000 operating software version 4.6.94 (Corbett Research) to determine the threshold cycle (CT) above the background for each reaction. The relative transcript amount of the target gene, calculated using standard curves of serial RNA dilutions, was normalized to that of beta-actin of the same RNA.

RNA interfering: siRNA oligonucleotides were designed for targeting the sequence of IRTKS (5'-AAGCACUGUG-GCUUUGCAAAC-3'; SEQ ID NO: 19) and Solt (5'-AA-CACUCACCGAUUCAAAUGC-3'; SEQ ID NO: 20). The target sequence (AATTCTCCGAACGTGTCACGT; SEQ ID NO: 21) which has 16 base overlap with *Thermotoga maritimia* section 21 of 136 of the complete genome was used as a negative control siRNA. siRNAs were synthesized by the silencer™ siRNA Construction Kit (Ambion, Texas, USA) following the manufacturer's protocol. siRNA transfection were performed in 24-well plates using the Oligofectamine™ (Invitrogen Corporation, CA, USA), Lipo-Fectamine™ 2000 (Invitrogen Corporation, CA, USA), or siPORT™ Amine (Ambion, Texas, USA), depending on the cell types.

Cell viability assay: The cell viability was determined by adding MTT (Sigma-Aldrich, MO, USA) to the cell cultures at a final concentration of 1 mg/ml. After 5 hr incubation at 37° C., the dark crystals formed were dissolved in DMSO and the amount was obtained by measuring the absorbance of the solution at 570/630 nm.

We found that the selected 4 genes were up-regulated in ovarian cancer tissue and cell lines (normal ovary and ovarian cancer RNA were purchased from BD Biosciences Clontech) using microarray and Quantitative real-time RT-PCR methods. These genes are listed in Table 1 and Sequence Listing.

Moreover, using the ovarian cell lines as the cell model, we found that inhibiting the expression of IRTKS or Solt could decrease the growth of ovarian cancer cells based on our RNAi experiment. Since IRTKS is one of the insulin receptor tyrosine kinase substrate and Solt is transcription factor related protein, both of them should be involved in the signal transduction pathway of cell growth or development. Based on our finding, IRTKS and Solt are potential therapeutic targets for ovarian cancer.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

TABLE 1

| Gene Name | SEQ ID NO (nucleotide sequence) | SEQ ID NO (amino acid sequence) | CDS |
| --- | --- | --- | --- |
| IRTKS: Insulin receptor tyrosine kinase substrate | 1 | 2 | 217 ... 1752 |
| Solt: SoxLZ/Sox6-binding protein Solt | 3 | 4 | 265 ... 1074 |
| Shax3: Snf7 homologue associated with Alix 3 | 5 | 6 | 179 ... 880 |
| WBSCR21: Williams Beuren syndrome chromosome region 21 | 7 | 8 | 63 ... 368 |

TABLE 2

| Gene Name | SEQ ID NO (nucleotide sequence) Forward Primer | SEQ ID NO (nucleotide sequence) Reverse Primer |
| --- | --- | --- |
| IRTKS: Insulin receptor tyrosine kinase substrate | 9 | 10 |
| Solt: SoxLZ/Sox6-binding protein Solt | 11 | 12 |
| Shax3: Snf7 homologue associated with Alix 3 | 13 | 14 |
| WBSCR21: Williams Beuren syndrome chromosome region 21 | 15 | 16 |

We claim:

1. A method of assessing whether a patient is afflicted with ovarian carcinoma, the method comprising a) determining the amount of a SEQ ID NO:1 marker in a patient ovarian tissue sample; b) determining the normal amount of the SEQ ID NO:1 marker in a control non-cancerous ovarian tissue sample; and c) comparing the amounts of the marker between the patient ovarian tissue sample and the control non-cancerous ovarian tissue sample, wherein a significant increase in the amount of the marker in the patient sample from the normal level is an indication that the patient is afflicted with ovarian carcinoma.

2. The method of claim 1 wherein the amount of the marker is determined in the patient sample and the non cancerous sample by hybridizing a polynucleotide expressed by the marker with an oligonucleotide or polynucleotide that is complementary to the polynucleotide expressed by the marker.

3. The method of claim 1 wherein the determination of the amount of the marker comprises performing a polymerase chain reaction.

4. The method of claim 1 wherein the determination of the amount of the marker comprises performing quantitative real-time reverse transcription-polymerase chain reaction.

5. The method of claim 1 wherein the determination of the amount of the marker comprises the use of a microarray.

* * * * *